United States Patent
Jiang et al.

(10) Patent No.: US 9,257,632 B2
(45) Date of Patent: Feb. 9, 2016

(54) PHYSICAL QUANTITY SENSOR AND PROCESS FOR PRODUCTION THEREOF

(75) Inventors: Yonggang Jiang, Himeji (JP); Kohei Higuchi, Himeji (JP); Hiroyuki Hamada, Himeji (JP); Kazusuke Maenaka, Himeji (JP)

(73) Assignee: JAPAN SCIENCE AND TECHNOLOGY AGENCY, Kawaguchi-Shi, Saitama (JP)

( * ) Notice: Subject to any disclaimer, the term of this patent is extended or adjusted under 35 U.S.C. 154(b) by 308 days.

(21) Appl. No.: 13/704,413

(22) PCT Filed: Jun. 22, 2011

(86) PCT No.: PCT/JP2011/064308
§ 371 (c)(1),
(2), (4) Date: Dec. 14, 2012

(87) PCT Pub. No.: WO2011/162305
PCT Pub. Date: Dec. 29, 2011

(65) Prior Publication Data
US 2013/0088124 A1 Apr. 11, 2013

(30) Foreign Application Priority Data
Jun. 22, 2010 (JP) ................. 2010-141923

(51) Int. Cl.
*H01L 41/04* (2006.01)
*H01L 41/113* (2006.01)
(Continued)

(52) U.S. Cl.
CPC .............. *H01L 41/1132* (2013.01); *G01L 1/18* (2013.01); *H01L 41/0474* (2013.01); *H01L 41/22* (2013.01); *H01L 41/332* (2013.01);
(Continued)

(58) Field of Classification Search
CPC .............. H01L 41/047; H01L 41/0471; H01L 41/0536; H01L 41/1132; H01L 41/1138
USPC .................................. 310/328, 324
See application file for complete search history.

(56) References Cited

U.S. PATENT DOCUMENTS

| | | | | |
|---|---|---|---|---|
| 4,431,935 A | * | 2/1984 | Rider | 310/331 |
| 7,721,397 B2 | * | 5/2010 | Chang et al. | 29/25.42 |
| 8,826,748 B2 | * | 9/2014 | Nakamura et al. | 73/862.473 |
| 2006/0028095 A1 | | 2/2006 | Maruyama et al. | |

(Continued)

OTHER PUBLICATIONS

European Search Report dated Jan. 9, 2015 in corresponding European Application No. 11 79 8187.
(Continued)

*Primary Examiner* — J. San Martin
(74) *Attorney, Agent, or Firm* — Nath, Goldberg & Meyer; Jerald L. Meyer; Stanley N. Protigal

(57) ABSTRACT

A physical quantity sensor (100), which can detect multiple physical quantities simultaneously has flexibility or bendability over the entire body thereof. The sensor (100) has a first electrode layer (2) formed on a substrate (1) and first and second piezoelectric elements (3a, 3b) arranged in parallel on the electrode layer (2). Two additional electrode layers (4a, 4b) are formed on the piezoelectric elements (3a, 3b). The substrate (1), the electrode layer (2), first piezoelectric element (3a), one of the additional electrode layers (4a) and protective layers (5a, 5b, 5c, 5d, 5e) constitute a first physical quantity detection unit (6), and the substrate (1), the first electrode layer (2), the second piezoelectric element (3b) and the other additional electrode layer (4b) (a fourth electrode layer) constitute a second physical quantity detection unit (7).

9 Claims, 7 Drawing Sheets

(51) Int. Cl.
*H01L 41/047* (2006.01)
*H01L 41/22* (2013.01)
*H01L 41/332* (2013.01)
*G01L 1/18* (2006.01)
*A61B 5/024* (2006.01)
*A61B 5/08* (2006.01)
*H01L 41/193* (2006.01)
*A61B 5/00* (2006.01)

(52) U.S. Cl.
CPC .............. *A61B5/02444* (2013.01); *A61B 5/08* (2013.01); *A61B 5/6832* (2013.01); *A61B 2503/40* (2013.01); *A61B 2562/0247* (2013.01); *A61B 2562/12* (2013.01); *H01L 41/193* (2013.01); *Y10T 29/42* (2015.01)

(56) References Cited

U.S. PATENT DOCUMENTS

2010/0194243 A1* 8/2010 Yoneyama .................... 310/338
2011/0121591 A1* 5/2011 Nishiwaki .................... 294/86.4
2011/0193363 A1* 8/2011 Nishiwaki .................... 294/86.4

OTHER PUBLICATIONS

Lee, et al., "Matched Piezoelectric Double Sensor/Actuator Pairs for Beam Motion Control", Smart Materials and Structures, vol. 12, No. 4, pp. 541-548, Aug. 2003.
Tzou, et al., "Theoretical Analysis of a Multi-Layered Thin Shell Coupled with Piezoelectric Shell Actuators for Distributed Vibration Controls", Journal of Sound and Vibration, vol. 132, No. 3, pp. 433-450, Aug. 1989.

* cited by examiner

PHYSICAL QUANTITY SENSOR AND PROCESS FOR PRODUCTION THEREOF

This is a National Phase Application filed under 35 U.S.C. 371 as a national stage of PCT/JP2011/064308 filed Jun. 22, 2011, and claims priority benefit from Japanese Application No. 2010-141923, filed Jun. 22, 2010, the content of each of which is hereby incorporated by reference in its entirety.

FIELD OF THE INVENTION

The present invention relates to a physical quantity sensor for measuring a plurality of physical quantities and a process for production thereof.

DESCRIPTION OF THE RELATED ART

As disclosed in Japanese Patent Laid-Open No. 2002-31574, a sensor is conventionally known which can detect a pressure, simultaneously detect both the sense of pressure and the sense of slip, and also detect projections and depressions on a surface.

However, in recent years, there has been a demand for a sensor that not only has a pressure detection function but also detects other physical quantities from an object and detects a condition of the object. For example, it is expected to simultaneously detect a pressure from the object and bending deflection of the object or the like using one sensor.

It is therefore an object of the present invention to provide a physical quantity sensor and process for production thereof capable of simultaneously detecting a plurality of physical quantities.

SUMMARY OF THE INVENTION (1) A physical quantity sensor of the present invention includes a first physical quantity detection section having a first electrode layer, a first piezoelectric element provided on the first electrode layer and a second electrode layer provided on the first piezoelectric element, and a second physical quantity detection section having a third electrode layer, a second piezoelectric element provided on the third electrode layer and a fourth electrode layer provided on the second piezoelectric element, wherein the first piezoelectric element is disposed so that a center line in a thickness direction of the first piezoelectric element substantially matches or matches a center line in a thickness direction of the first physical quantity detection section, and the second piezoelectric element is disposed so that a center line in a thickness direction of the second piezoelectric element is disposed eccentrically with respect to a center line in a thickness direction of the second physical quantity detection section.

According to the configuration in (1) above, a plurality of physical quantities can be simultaneously detected. For example, it is possible to simultaneously detect a pressure from the object using the first piezoelectric element and bending deflection of the object using the second piezoelectric element. Therefore, the physical quantity sensor of the present invention can be used, for example, as a contact sensor.

(2) In the physical quantity sensor in (1) above, the first physical quantity detection section and the second physical quantity detection section are arranged side by side, and part of the first electrode layer and part of the third electrode layer may be connected together so as to form one electrode layer.

According to the configuration in (2) above, it is possible to reduce the thickness of the sensor and form an electrode common to the first physical quantity detection section and the second physical quantity detection section through one process, and thereby easily produce the sensor.

(3) In the physical quantity sensor in (1) above, the second physical quantity detection section may be laminated on at least one side of the first physical quantity detection section via a flexible insulating layer.

According to the configuration in (3) above, since the first physical quantity detection section and the second physical quantity detection section can be integrated into one unit, it is possible to realize a smaller physical quantity sensor. Furthermore, laminating the piezoelectric element of the second physical quantity detection section so as to be arranged on both sides of the piezoelectric element of the first physical quantity detection section may double the sensor sensitivity in the second physical quantity detection section.

(4) In the physical quantity sensor in (2) above, the first electrode on the first piezoelectric element side may be fixed to a substrate and the second piezoelectric element may constitute a cantilever oscillatable in a predetermined direction by external vibration.

According to the configuration in (4) above, it is possible to detect a pressure from the object using the first piezoelectric element and also detect vibration of the object using the second piezoelectric element.

(5) In the physical quantity sensor in (1) to (4) above, a polydimethyl siloxane (hereinafter, represented by "PDMS") substrate may be preferably provided on at least part of the surface.

According to the configuration in (5) above, since the PDMS substrate has biocompatibility, it is possible to paste the present physical quantity sensor to the skin or the like of an animal via the PDMS substrate for a long time and thereby obtain biological information such as pulsation, heart beat and respiration.

(6) A process for producing a physical quantity sensor of the present invention is a process for producing the physical quantity sensor in (2) above, including a piezoelectric element forming step of laminating and then etching a piezoelectric element layer on the one electrode layer to form the first piezoelectric element and the second piezoelectric element, and an electrode layer forming step of laminating and then etching a conductive layer on the first piezoelectric element and the second piezoelectric element to form the third electrode layer on the first piezoelectric element and form the fourth electrode layer on the second piezoelectric element.

According to the configuration in (6) above, the physical quantity sensor in (2) above can be easily produced. Particularly since an electrode common to the first physical quantity detection section and the second physical quantity detection section can be formed through one process, it is possible to easily produce the physical quantity sensor in (2) above.

DETAILED DESCRIPTION OF THE PREFERRED EMBODIMENTS

First Embodiment

Hereinafter, a physical quantity sensor according to a first embodiment of the present invention will be described with reference to the accompanying drawings.

Figure 1:
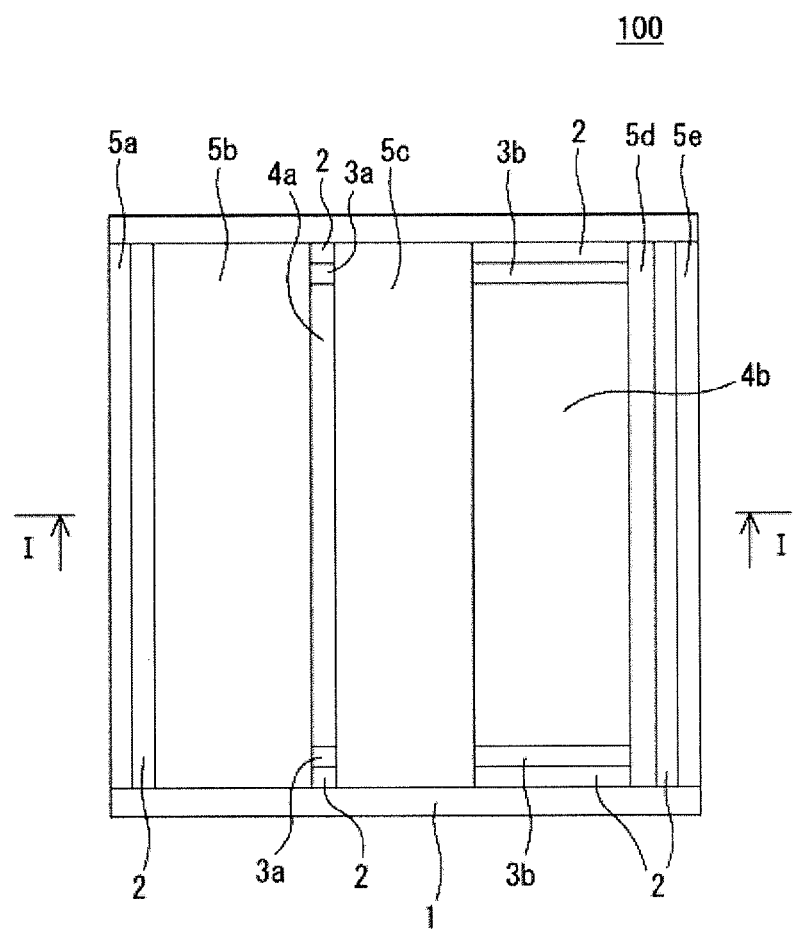
FIG. 1 is a plan view of a physical quantity sensor according to a first embodiment of the present invention.
Figure 2:
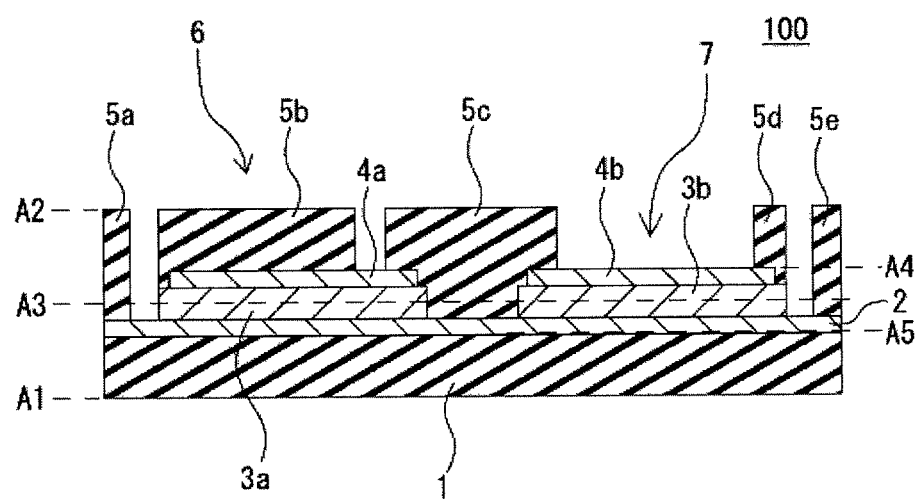
FIG. 2 is a cross-sectional view along line I-I shown by an arrow in FIG. 1.

As shown in FIG. 1 and FIG. 2, a physical quantity sensor 100 according to the present embodiment is provided with a substrate 1, an electrode layer 2 formed on the substrate 1, a piezoelectric element 3a and a piezoelectric element 3b disposed side by side on the electrode layer 2, electrode layers 4a and 4b formed on the piezoelectric elements 3a and 3b and protective layers 5a, 5b, 5c, 5d and 5e that protect the electrode layer 2, the piezoelectric elements 3a and 3b and the electrode layers 4a and 4b. Furthermore, the substrate 1, the electrode layer 2, the piezoelectric element 3a (first piezoelectric element), the electrode layer 4a (third electrode layer) and the protective layers 5a, 5b, 5c, 5d and 5e constitute a first physical quantity detection section 6, and the substrate 1, the electrode layer 2, the piezoelectric element 3b (second piezoelectric element) and the electrode layer 4b (fourth electrode layer) constitute a second physical quantity detection section 7.

The substrate 1 is made of a flexible insulating material. For the substrate 1, any material may be used according to the purpose as long as it has flexibility. For example, when the physical quantity sensor 100 is used pasted to a living body, PDMS may be used in consideration of biocompatibility.

The electrode layers 2, 4a and 4b are made of a flexible conductive material and, for example, copper, silver, gold, nickel-copper alloy or conductive polymer may be used.

The piezoelectric elements 3a and 3b are made of a flexible piezoelectric material. An example thereof may be piezoelectric polymer of PVDF (polyvinylidene fluoride). As shown in FIG. 2, a center line in the thickness direction of the piezoelectric element 3a matches a center position (center line in the thickness direction of the first physical quantity detection section 6) A3 between a bottom surface position A1 and a top surface position A2 of the physical quantity sensor 100. A center line in the thickness direction of the piezoelectric element 3b is disposed eccentrically with respect to a center position (center line in the thickness direction of the second physical quantity detection section 7) A5 between the bottom surface position A1 and a top surface position A4 of the second physical quantity detection section.

The protective layers 5a, 5b, 5c, 5d and 5e are made of a flexible insulating material. For the protective layers 5a, 5b, 5c, 5d and 5e, any material may be used as long as it is flexible according to the purpose as in the case of the substrate 1. For example, when the physical quantity sensor 100 is used as a pasted sensor to a living body, PDMS may be used in consideration of biocompatibility.

Next, operation of the physical quantity sensor 100 will be described. Here, for example, suppose the physical quantity sensor 100 shown in FIG. 2 is bent so as to warp in a convex form to an extent that it is not plastically deformed with the center of the surface of the protective layer 5c as a vertex. In this case, although stress of bending operation is added to the piezoelectric element 3a in the first physical quantity detection section 6, since the center line in the thickness direction of the piezoelectric element 3a matches the center position (the center line in the thickness direction of the first physical quantity detection section 6) A3 between the bottom surface position A1 and the top surface position A2, stress deformation of the piezoelectric element 3a becomes symmetric on the top surface position A2 side and the bottom surface position A1 side, causing surface charges generated on the top and bottom surfaces to cancel out each other. That is, the first physical quantity detection section 6 does not detect a bending force. In contrast, in the second physical quantity detection section 7, since the center line in the thickness direction of the piezoelectric element 3b is disposed eccentrically with respect to the center position (center line in the thickness direction of the second physical quantity detection section 7) A5 between the bottom surface position A1 and the top surface position A4 of the second physical quantity detection section 7, stress deformation of the piezoelectric element 3b becomes asymmetric on the top surface position A4 side and the bottom surface position A1 side, preventing surface charges generated on the top and bottom surfaces of the piezoelectric element 3b from canceling out each other. Therefore, by measuring a voltage value generated in the second physical quantity detection section 7, it is possible to detect the degree of the bending force as a value. In the case where the physical quantity sensor 100 shown in FIG. 2 is bent so as to warp in a concave form to an extent that it is not plastically deformed with the center of the surface of the substrate 1 as a vertex, it is likewise possible to detect the degree of the bending force as a value.

Next, in the physical quantity sensor 100 shown in FIG. 2, suppose, for example, both ends of the substrate 1 are fixed and the surfaces of the protective layers 5a, 5b, 5c, 5d and 5e are uniformly pressed from above downward in FIG. 2. In this case, the piezoelectric element 3a is deformed by receiving pressure from the protective layers 5b and 5c, and therefore surface charges generated on the top and bottom surfaces of the piezoelectric element 3a do not cancel out each other. Therefore, by measuring a voltage value generated in the first physical quantity detection section 6, it is possible to detect the degree of pressure applied to the physical quantity sensor 100 as a value. In the physical quantity sensor 100 shown in FIG. 2, the protective layers 5a and 5e are fixed and when the surface of the substrate 1 is uniformly pressed upward from below in FIG. 2, it is likewise possible to detect the degree of pressure applied to the physical quantity sensor 100 as a value. Here, the piezoelectric element 3b is also naturally pressed from the protective layers 5c and 5d and receives some influence. If the degree of influence of the pressure from the protective layers 5c and 5d is measured beforehand and a correction is made by subtracting a detection value about the pressure from the detection value about the force of bending operation, it is possible to make a setting so as to receive no influence from the protective layers 5c and 5d.

Figure 3:
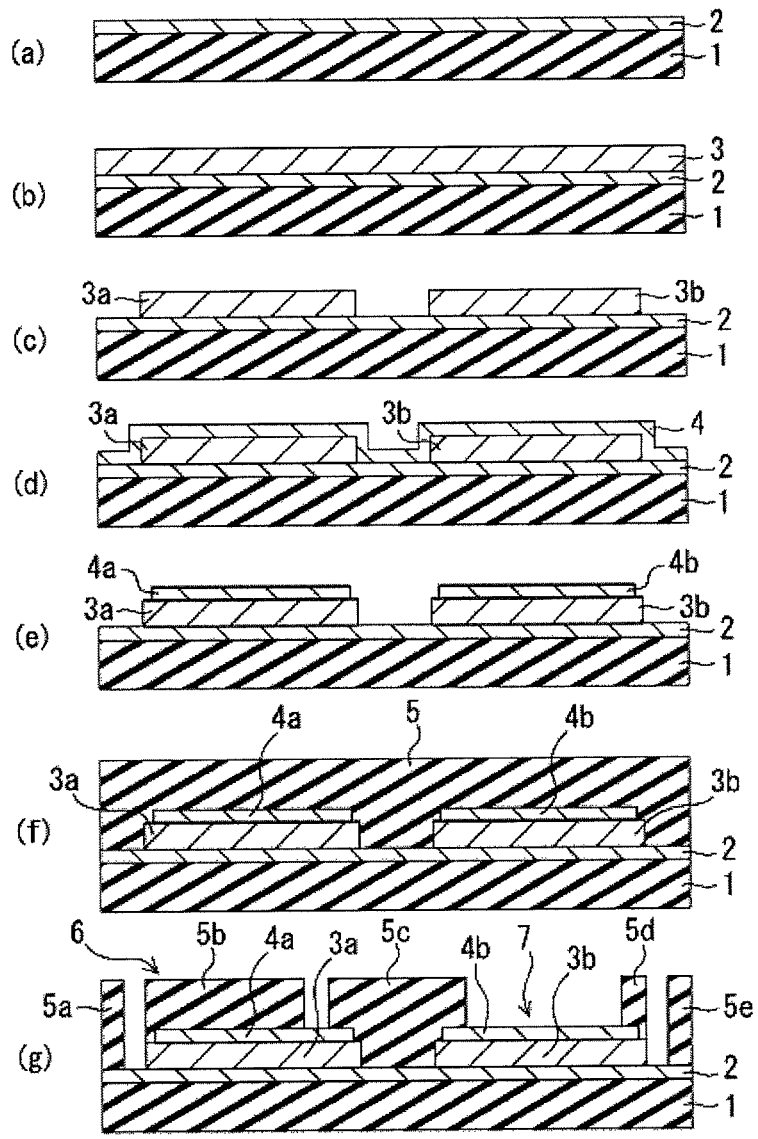
FIG. 3 is a diagram sequentially illustrating production steps of the physical quantity sensor shown in FIG. 1.

Next, a process for producing the physical quantity sensor 100 will be described using FIG. 3. First, a piezoelectric element layer 3 is laminated on the electrode layer 2 formed on the substrate 1 through sputtering or the like (see FIGS. 3 (a) and (b)). Next, the laminated piezoelectric element layer 3 is etched to form the piezoelectric element 3a and the piezoelectric element 3b through patterning (piezoelectric element forming step: see FIG. 3(c)). Next, a conductive layer 4 is laminated on the piezoelectric element 3a and the piezoelectric element 3b through sputtering or the like (see FIG. 3(d)) and then etched to form the electrode layer 4a on the piezoelectric element 3a and form the electrode layer 4b on the piezoelectric element 3b (electrode layer forming step: see FIG. 3(e)). An insulating material layer is then laminated from the electrode layer 4a and 4b sides through sputtering or the like (see FIG. 3 (f)) and then etched to form the protective layers 5a, 5b, 5c, 5d and 5e through patterning (see FIG. 3 (g)). This completes the physical quantity sensor 100.

The physical quantity sensor 100 of the present embodiment can simultaneously detect a plurality of physical quantities. That is, the piezoelectric element 3a can detect pressure from an object and the piezoelectric element 3b can detect bending deflection of the object at the same time. Therefore, the physical quantity sensor 100 can be used, for example, as a contact sensor.

Furthermore, since the electrode layer 2 is commonly used for the first physical quantity detection section 6 and the second physical quantity detection section 7, the physical quantity sensor 100 can be made thinner. Furthermore, since the electrode layer 2 commonly used for the first physical quantity detection section 6 and the second physical quantity detection section 7 can be formed through one process, the physical quantity sensor 100 can be produced easily.

Furthermore, when a PDMS substrate is used for the substrate 1, since the PDMS substrate has biocompatibility, the physical quantity sensor 100 including the PDMS substrate can be pasted to the skin or the like of an animal for a long time and it is possible to obtain biological information such as pulsation, heart beat and respiration. The same applies to a case where PDMS is used for the substrate or the like in the following embodiments and modification example.

Second Embodiment

Next, a physical quantity sensor according to a second embodiment of the present invention will be described. Regions denoted by reference numerals 11, 12, 13a and 14a in the present embodiment are similar to the regions denoted by reference numerals 1, 2, 3a and 4a in the first embodiment respectively, and therefore descriptions thereof may be omitted.

Figure 4:
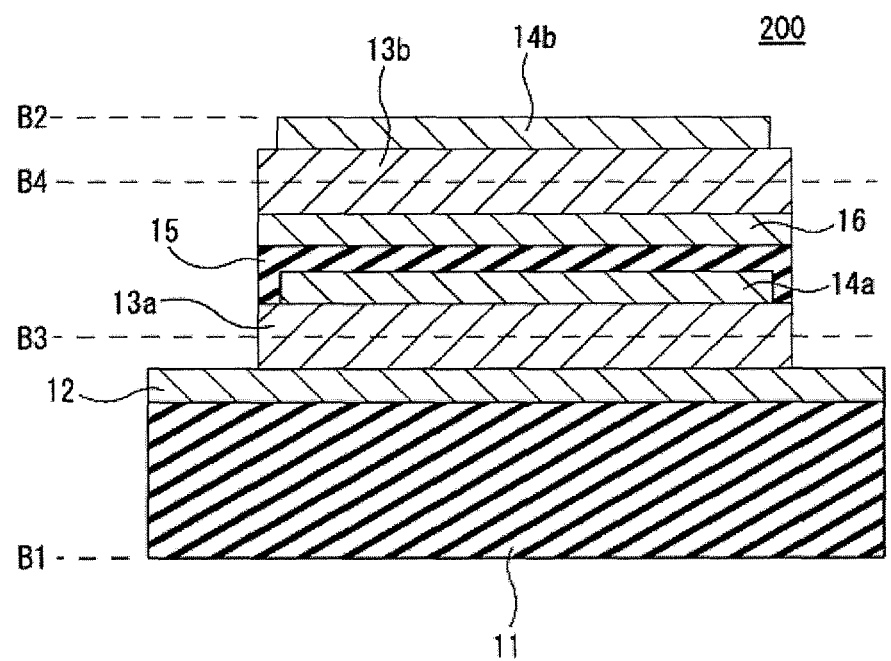
FIG. 4 is a cross-sectional view of a physical quantity sensor according to a second embodiment of the present invention.

As shown in FIG. 4, a physical quantity sensor 200 according to the present embodiment is provided with a substrate 11, an electrode layer 12 formed on the substrate 11, a piezoelectric element 13a formed on the electrode layer 12, an electrode layer 14a formed on the piezoelectric element 13a, an insulating layer 15 formed on the piezoelectric element 13a and the electrode layer 14a, an electrode layer 16 formed on the insulating layer 15, a piezoelectric element 13b formed on the electrode layer 16 and an electrode layer 14b formed on the piezoelectric element 13b. A first physical quantity detection section includes the electrode layer 12 (first electrode layer), the piezoelectric element 13a (first piezoelectric element) and the electrode layer 14a (third electrode layer) as main parts, and includes the regions other than the piezoelectric element 13a in the physical quantity sensor 200 as a layer for adjusting the position at which the piezoelectric element 13a is disposed. Furthermore, a second physical quantity detection section includes the electrode layer 16 (second electrode layer), the piezoelectric element 13b (second piezoelectric element) and the electrode layer 14b (fourth electrode layer) as main parts, and includes the regions other than the piezoelectric element 13b in the physical quantity sensor 200 as a layer for adjusting the position at which the piezoelectric element 13b is disposed.

The insulating layer 15 is made of a flexible insulating material. For the insulating layer 15, as in the case of the substrate 11, any material may be used according to the purpose as long as it is flexible.

As in the case of the electrode layer 14a, the electrode layer 14b and the electrode layer 16 are made of a flexible conductive material and, for example, copper, silver, gold, nickel-copper alloy or conductive polymer may be used.

As in the case of the piezoelectric element 13a, the piezoelectric element 13b is made of a flexible piezoelectric material. An example thereof may be piezoelectric polymer of PVDF (polyvinylidene fluoride). As shown in FIG. 4, a center line in the thickness direction of the piezoelectric element 13a matches a center position (center line in the thickness direction of the first physical quantity detection section) B3 between a bottom surface position B1 and a top surface position B2 of the first physical quantity detection section. A center line in the thickness direction B4 of the piezoelectric element 13b is disposed eccentrically with respect to a center position (center line in the thickness direction of the second physical quantity detection section) B3 between the bottom surface position B1 and the top surface position B2 of the second physical quantity detection section.

Next, operation of the physical quantity sensor 200 will be described. Here, suppose, for example, the physical quantity sensor 200 shown in FIG. 4 is bent so as to warp in a convex form to an extent that it is not plastically deformed with the center of the surface of the electrode layer 14b as a vertex. In this case, although stress of bending operation is added to the piezoelectric element 13a in the first physical quantity detection section, since the center line in the thickness direction of the piezoelectric element 13a matches the center position (center line in the thickness direction of the first physical quantity detection section) B3 between the bottom surface position B1 and the top surface position B2, stress deformation of the piezoelectric element 13a becomes symmetric on the top surface position B2 side and the bottom surface position B1 side, causing surface charges generated on the top and bottom surfaces of the piezoelectric element 13a to cancel out each other. That is, the first physical quantity detection section does not detect a bending force. In contrast, in the second physical quantity detection section, since the center line in the thickness direction of the piezoelectric element 13b is disposed eccentrically with respect to the center position (center line in the thickness direction of the second physical quantity detection section) B3 between the bottom surface position B1 and the top surface position B2 of the second physical quantity detection section, stress deformation of the piezoelectric element 13b becomes asymmetric on the top surface position B2 side and the bottom surface position B1 side, preventing surface charges generated on the top and bottom surfaces of the piezoelectric element 13b from canceling out each other. Therefore, by measuring a voltage value generated in the second physical quantity detection section, it is possible to detect the degree of the bending force as a value. In the case where the physical quantity sensor 200 shown in FIG. 4 is bent so as to warp in a concave form to an extent that it is not plastically deformed with the center of the surface of the substrate 11 as a vertex, it is likewise possible to detect the degree of the bending force as a value.

Next, in the physical quantity sensor 200 shown in FIG. 4, suppose, for example, both ends of the substrate 11 are fixed and the surface of the electrode layer 14b is uniformly pressed from above downward in FIG. 4. In this case, the piezoelectric element 13a is deformed by receiving pressure from the electrode layer 14b side, and therefore surface charges generated on the top and bottom surfaces of the piezoelectric element 13a do not cancel out each other. Therefore, by measuring a voltage value generated in the first physical quantity detection section, it is possible to detect the degree of pressure applied to the physical quantity sensor 200 as a value. In the physical quantity sensor 200 shown in FIG. 4, both ends of the electrode layer 14b are fixed and when the surface of the substrate 11 is uniformly pressed upward from below in FIG. 4, it is likewise possible to detect the degree of pressure applied to the physical quantity sensor 200 as a value. Here, the piezoelectric element 13b is also naturally pressed and receives some influence, but if the degree of influence of pressure is measured beforehand and a correction is made by subtracting a detection value about the pressure from the detection value about the force of bending operation, it is possible to make a setting so as to receive no influence of the pressure.

Next, a process for producing the physical quantity sensor 200 will be described. As in the case of the process for producing the physical quantity sensor 100 according to the above-described first embodiment, the respective regions are laminated on the substrate 11 through patterning using sputtering, etching or the like. To be more specific, the piezoelectric element layer is laminated on the electrode layer 12 formed on the substrate 11 through sputtering or the like first, and then etched to form the piezoelectric element 13a through patterning. Next, a conductive layer is laminated from the piezoelectric element 13a side through sputtering or the like and etched to form the electrode layer 14a on the piezoelectric element 13a. Next, an insulating material layer is laminated from the electrode layer 14a side through sputtering or the like, and then etched to form the insulating layer 15. Next, a conductive layer is laminated from the insulating layer 15 side through sputtering or the like, and then etched to form the electrode layer 16 on the insulating layer 15. Next, a piezoelectric material layer is laminated from the electrode layer 16 side through sputtering or the like, and then etched to form the piezoelectric element 13b. A conductive layer is then laminated from the piezoelectric element 13b side through sputtering or the like, and then etched to form the electrode layer 14b on the piezoelectric element 13b, and the physical quantity sensor 200 is thereby completed.

The physical quantity sensor 200 of the present embodiment can simultaneously detect a plurality of physical quantities. That is, the piezoelectric element 13a can detect pressure from an object and the piezoelectric element 13b can detect bending deflection at the same time. Therefore, the physical quantity sensor 200 can be used, for example, as a contact sensor.

Furthermore, the first physical quantity detection section and the second physical quantity detection section can be integrated into one unit, and it is thereby possible to realize a smaller physical quantity sensor 200.

Third Embodiment

Next, a physical quantity sensor according to a third embodiment of the present invention will be described. Since regions denoted by reference numerals 22, 23a and 24a in the present embodiment are similar to the regions denoted by reference numerals 2, 3a and 4a in the first embodiment, descriptions thereof may be omitted.

Figure 5:
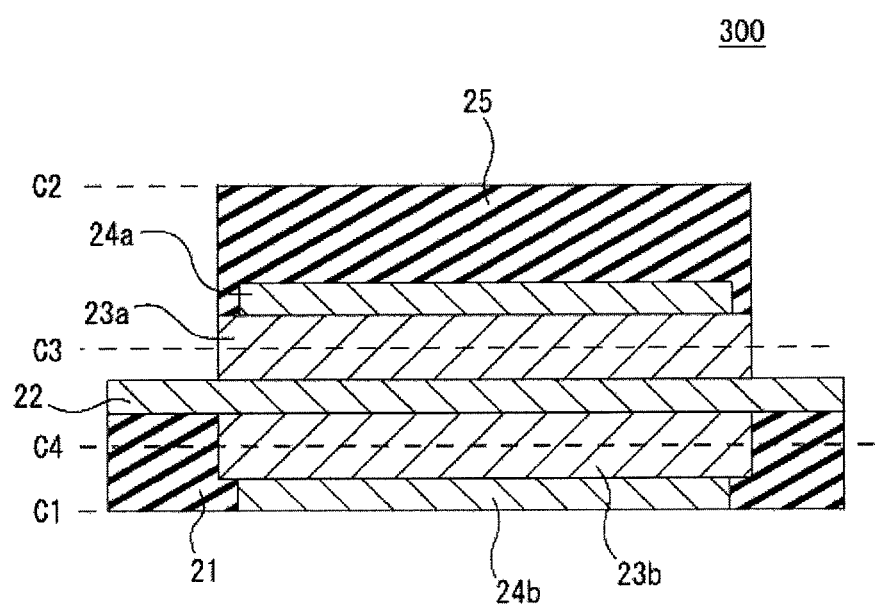
FIG. 5 is a cross-sectional view of a physical quantity sensor according to a third embodiment of the present invention.

As shown in FIG. 5, a physical quantity sensor 300 according to the present embodiment is provided with a substrate 21, an electrode layer 22 formed on the substrate 21, a piezoelectric element 23a formed on the electrode layer 22, an electrode layer 24a formed on the piezoelectric element 23a, a protective layer 25 formed on the piezoelectric element 23a and the electrode layer 24a, a piezoelectric element 23b formed below the electrode layer 22 and embedded in the substrate 21, and an electrode layer 24b formed below the piezoelectric element 23b and embedded in the substrate 21. A first physical quantity detection section includes the electrode layer 22, the piezoelectric element 23a (first piezoelectric element) and the electrode layer 24a (third electrode layer) as main components and also includes regions other than the piezoelectric element 23a in the physical quantity sensor 300 (except the substrate 21) as a layer for adjusting the position at which the piezoelectric element 23a is disposed. Furthermore, a second physical quantity detection section includes the electrode layer 22, the piezoelectric element 23b (second piezoelectric element) and the electrode layer 24b (fourth electrode layer) as main components and also includes regions other than the piezoelectric element 23b in the physical quantity sensor 300 (except the substrate 21) as a layer for adjusting the position at which the piezoelectric element 23b is disposed.

The substrate 21 is made of a flexible insulating material. For the substrate 21, any material may be used according to the purpose as long as it is flexible. For example, when the physical quantity sensor 300 is used pasted to a living body, PDMS may be used in consideration of biocompatibility.

The piezoelectric element 23b is formed using a material similar to that of the piezoelectric element 23a and disposed at a position opposite to the piezoelectric element 23a centered on the electrode layer 22. As shown in FIG. 5, the center line in the thickness direction of the piezoelectric element 23a matches the center position (center line in the thickness direction of the first physical quantity detection section) C3 between the bottom surface position C1 and the top surface position C2 of the first physical quantity detection section. The center line in the thickness direction C4 of the piezoelectric element 23b is disposed eccentrically with respect to the center position (center line in the thickness direction of the second physical quantity detection section) C3 between the bottom surface position C1 and the top surface position C2 of the second physical quantity detection section.

The electrode layer 24b is formed using a material similar to that of the electrode layer 24a and is disposed at a position opposite to the electrode layer 24a centered on the electrode layer 22.

The protective layer 25 is made of a flexible insulating material. For the protective layer 25, any material may be used according to the purpose as long as it is flexible as in the case of the substrate 21.

Next, operation of the physical quantity sensor 300 will be described. Here, suppose the physical quantity sensor 300 shown in FIG. 5 is bent so as to warp in a convex form to an extent that it is not plastically deformed with the center of the surface of the protective layer 25 as a vertex. In this case, although stress of bending operation is added to the piezoelectric element 23a in the first physical quantity detection section, since the center line in the thickness direction of the piezoelectric element 23a matches the center position (the center line in the thickness direction of the first physical quantity detection section) C3 between the bottom surface position C1 and the top surface position C2, stress deformation of the piezoelectric element 23a becomes symmetric on the top surface position C2 side and the bottom surface position C1 side, causing surface charges generated on the top and bottom surfaces of the piezoelectric element 23a to cancel out each other. That is, the first physical quantity detection section does not detect a bending force. In contrast, in the second physical quantity detection section, since the center line in the thickness direction of the piezoelectric element 23b is disposed eccentrically with respect to the center position (center line in the thickness direction of the second physical quantity detection section) C3 between the bottom surface position C1 and the top surface position C2 of the second physical quantity detection section, stress deformation of the piezoelectric element 23b becomes asymmetric on the top surface position C2 side and the bottom surface position C1 side, preventing surface charges generated on the top and bottom surfaces of the piezoelectric element 23b from canceling out each other. Therefore, by measuring a voltage value generated in the second physical quantity detection section, it is possible to detect the degree of the bending force as a value. In the case where the physical quantity sensor 300 shown in FIG. 5 is bent so as to warp in a concave form to an extent that it is not plastically deformed with the center of the surface of the electrode layer 24b as a vertex, it is likewise possible to detect the degree of the bending force as a value.

Next, in the physical quantity sensor 300 shown in FIG. 5, both ends of the substrate 21 are fixed and suppose the surface of the protective layer 25 is uniformly pressed from above downward in FIG. 5. In this case, the piezoelectric element 23a is deformed by receiving pressure from the protective layer 25 side, and therefore surface charges generated on the top and bottom surfaces of the piezoelectric element 23a do not cancel out each other. Therefore, by measuring a voltage value generated in the first physical quantity detection section, it is possible to detect the degree of pressure applied to the physical quantity sensor 300 as a value. Both ends of the protective layer 25 are fixed and when the surfaces of the substrate 21 and the electrode layer 24b are uniformly pressed upward from below in FIG. 5, it is likewise possible to detect the degree of pressure applied to the physical quantity sensor 300 as a value. Here, the piezoelectric element 23b is also naturally pressed and receives some influence. If the degree of influence of pressure is measured beforehand and a correction is made by subtracting a detection value about the pressure from the detection value about the force of bending operation, it is possible to make a setting so as to receive no influence of the pressure.

Next, a process for producing the physical quantity sensor 300 will be described. As in the case of the process for producing the physical quantity sensor 100 of the above-described first embodiment, the respective regions are laminated and formed through patterning using sputtering, etching or the like. To be more specific, the electrode layer 24b is formed first, the substrate 21 is laminated so as to cover one side of the electrode layer 24b, the substrate 21 is then etched to form a dent for the piezoelectric element 23a. Next, a piezoelectric material is embedded in the dent through sputtering to form the piezoelectric element 23a. Next, the electrode layer 22 and the piezoelectric element layer are laminated on the substrate 21 and the piezoelectric element 23a respectively through sputtering or the like and etched to form the piezoelectric element 23a through patterning. Next, a conductive layer is laminated from the piezoelectric element 23a side through sputtering or the like and then etched to form the electrode layer 24a on the piezoelectric element 23a through patterning. Next, the protective layer 25 is laminated on the piezoelectric element 23a and the electrode layer 24a through sputtering or the like, and the physical quantity sensor 300 is thereby completed.

According to the physical quantity sensor 300 of the present embodiment, it is possible to simultaneously detect a plurality of physical quantities. That is, it is possible to detect pressure from the object through the piezoelectric element 23a and detect bending operation displacement of the object through the piezoelectric element 23b at the same time. Therefore, the physical quantity sensor 300 can be used, for example, as a contact sensor.

Furthermore, since the first physical quantity detection section and the second physical quantity detection section can be integrated into one unit, it is possible to realize a smaller physical quantity sensor 300. Furthermore, since the electrode layer 22 is shared between the first physical quantity detection section and the second physical quantity detection section, the physical quantity sensor 300 can be made thinner. Furthermore, since the electrode layer 22 commonly used for the first physical quantity detection section and the second physical quantity detection section can be formed through one process, the physical quantity sensor 300 can be produced easily.

Fourth Embodiment

Next, a physical quantity sensor according to a fourth embodiment of the present invention will be described. Since regions denoted by reference numerals 32, 33a and 34a in the present embodiment are similar to the regions denoted by reference numerals 2, 3a and 4a in the first embodiment, descriptions thereof may be omitted. Furthermore, regions denoted by reference numerals 33b and 34b in the present embodiment are similar to the regions denoted by reference numerals 23a and 24b in the third embodiment respectively, descriptions thereof may be omitted.

Figure 6:
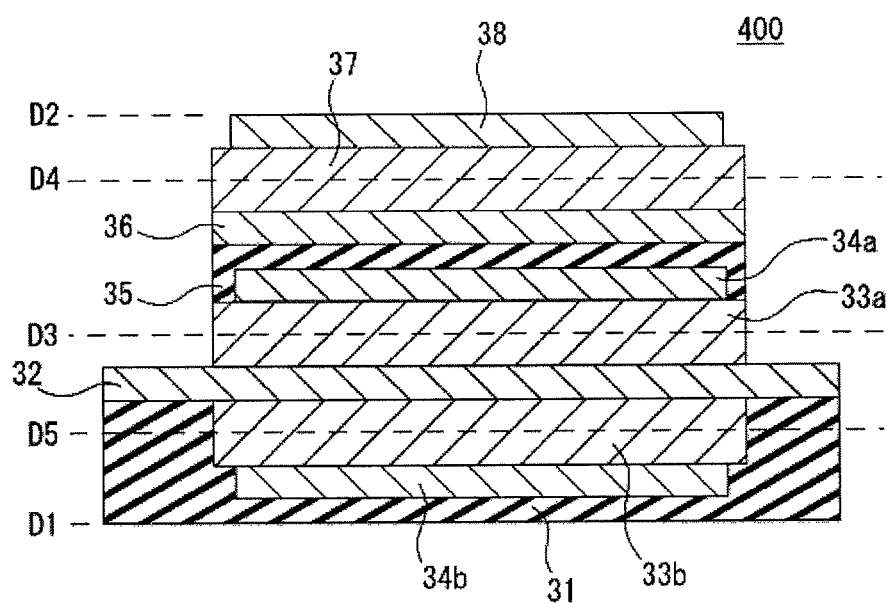
FIG. 6 is a cross-sectional view of a physical quantity sensor according to a fourth embodiment of the present invention.

As shown in FIG. 6, a physical quantity sensor 400 according to the present embodiment is provided with a substrate 31, an electrode layer 32 formed on the substrate 31, a piezoelectric element 33a formed on electrode layer 32, an electrode layer 34a formed on the piezoelectric element 33a, an insulating layer 35 formed on the piezoelectric element 33a and the electrode layer 34a, an electrode layer 36 formed on the insulating layer 35, a piezoelectric element 37 formed on the electrode layer 36, an electrode layer 38 formed on the piezoelectric element 37, a piezoelectric element 33b formed below the electrode layer 32 and embedded in the substrate 31 and an electrode layer 34b formed below the piezoelectric element 33b and embedded in the substrate 31. A first physical quantity detection section includes the electrode layer 32, the piezoelectric element 33a (first piezoelectric element) and the electrode layer 34a (third electrode layer) as main components and also includes regions other than the piezoelectric element 33a in the physical quantity sensor 400 (except the substrate 21) as a layer for adjusting a position at which the piezoelectric element 33a is disposed. Furthermore, a second physical quantity detection section includes the electrode layer 32, the piezoelectric element 33b and the electrode layer 34b as a first main section and includes the electrode layer 36, the piezoelectric element 37 (second piezoelectric element) and the electrode layer 38 (fourth electrode layer) as a second main section. Furthermore, the piezoelectric element 33b in the first main section uses regions other than the piezoelectric element 33b in the physical quantity sensor 400 as a layer for adjusting a position at which the piezoelectric element 33b is disposed. Furthermore, the piezoelectric element 37 in the second main section uses regions other than the piezoelectric element 37 in the physical quantity sensor 400 as a layer for adjusting a position at which the piezoelectric element 37 is disposed.

The substrate 31 is made of a flexible insulating material. For the substrate 31, any material may be used according to the purpose as long as it is flexible. For example, when the physical quantity sensor 400 is used pasted to a living body, PDMS may be used in consideration of biocompatibility.

The piezoelectric element 33b is formed using a material similar to that of the piezoelectric element 33a and disposed at a position opposite to the piezoelectric element 33a centered on the electrode layer 32. As shown in FIG. 6, the center line in the thickness direction of the piezoelectric element 33a matches the center position (center line in the thickness direction of the first physical quantity detection section) D3 between the bottom surface position D1 and the top surface position D2 of the first physical quantity detection section. The center line in the thickness direction D4 of the piezoelectric element 37 is disposed eccentrically with respect to the center position (center line in the thickness direction of the second physical quantity detection section) D3 between the bottom surface position D1 and the top surface position D2 of the second physical quantity detection section. Furthermore, the center line in the thickness direction D5 of the piezoelectric element 33b is disposed eccentrically with respect to the center position (center line in the thickness direction of the second physical quantity detection section) D3 between the bottom surface position D1 and the top surface position D2 of the second physical quantity detection section.

The insulating layer 35 is made of a flexible insulating material. For the insulating layer 35, any material may be used according to the purpose as long as it is flexible as in the case of the substrate 31.

Next, operation of the physical quantity sensor 400 will be described. Here, suppose the physical quantity sensor 400 shown in FIG. 6 is bent so as to warp in a convex form to an extent that it is not plastically deformed with the center of the surface of the electrode layer 38 as a vertex. In this case, although stress of bending operation is added to the piezoelectric element 33a in the first physical quantity detection section, since the center line in the thickness direction of the piezoelectric element 33a matches the center position (the center line in the thickness direction of the first physical quantity detection section) D3 between the bottom surface position D1 and the top surface position D2, stress deformation of the piezoelectric element 33a becomes symmetric on the top surface position D2 side and the bottom surface position D1 side, causing surface charges generated on the top and bottom surfaces of the piezoelectric element 33a to cancel out each other. That is, the first physical quantity detection section does not detect a bending force. In contrast, in the second physical quantity detection section, since the center line in the thickness direction of the piezoelectric element 33b is disposed eccentrically with respect to the center position (center line in the thickness direction of the second physical quantity detection section) D3 between the bottom surface position D1 and the top surface position D2 of the second physical quantity detection section, stress deformation of the piezoelectric element 33b becomes asymmetric on the top surface position D2 side and the bottom surface position D1 side, preventing surface charges generated on the top and bottom surfaces of the piezoelectric element 33b from canceling out each other. Therefore, by measuring a voltage value generated in the second physical quantity detection section, it is possible to detect the degree of the bending force as a value. In the case where the physical quantity sensor 400 shown in FIG. 6 is bent so as to warp in a concave form to an extent that it is not plastically deformed with the center of the surface of the electrode layer 34b as a vertex, it is likewise possible to detect the degree of the bending force as a value.

Next, in the physical quantity sensor 400 shown in FIG. 6, suppose, for example, both ends of the substrate 31 are fixed and the surface of the electrode layer 38 is uniformly pressed downward from above in FIG. 6. In this case, the piezoelectric element 33a is deformed by receiving pressure from the electrode layer 38 side, and therefore surface charges generated on the top and bottom surfaces of the piezoelectric element 33a do not cancel out each other. Therefore, by measuring a voltage value generated in the first physical quantity detection section, it is possible to detect the degree of pressure applied to the physical quantity sensor 400 as a value. Both ends of the electrode layer 38 are fixed and when the surface of the substrate 31 is uniformly pressed upward from below in FIG. 6, it is likewise possible to detect the degree of pressure applied to the physical quantity sensor 400 as a value. Here, the piezoelectric elements 33b and 37 are also naturally pressed and receive some influence. If the degree of influence of the pressure is measured beforehand and a correction is made by subtracting a detection value about the pressure from the detection value about the force of bending operation, it is possible to make a setting so as to receive no influence of the pressure.

Next, a process for producing the physical quantity sensor 400 will be described. As in the case of the process for producing the physical quantity sensor 100 in the above-described first embodiment, the respective regions are laminated and formed through patterning using sputtering, etching or the like. To be more specific, the substrate 31 is etched first to form a dent for the electrode layer 34b and the piezoelectric element 33a. Next, a conductive material and a piezoelectric material are sequentially embedded in the above-described predetermined dent through sputtering to form the electrode layer 34b and the piezoelectric element 23a in that order. Next, the electrode layer 32 and the piezoelectric element layer are laminated on the substrate 31 and the piezoelectric element 33a respectively through sputtering or the like, and then etched to form the piezoelectric element 33a through patterning. Next, a conductive layer is laminated from the piezoelectric element 33a side through sputtering or the like, then etched to form the electrode layer 34a on the piezoelectric element 33a through patterning. Next, the insulating layer 35 is laminated on the piezoelectric element 33a and the electrode layer 34a through sputtering or the like and then the electrode layer 36 is laminated on the insulating layer 35. Next, the piezoelectric element 37 is laminated on the electrode layer 36 through sputtering or the like and then a conductive layer is laminated from the piezoelectric element 33a side through sputtering or the like. Then, the conductive layer is etched to form the electrode layer 38 on the piezoelectric element 37 through patterning, and the physical quantity sensor 400 is thereby completed.

According to the physical quantity sensor 400 of the present embodiment, a plurality of physical quantities can be simultaneously detected. That is, the piezoelectric element 33a can detect pressure from the object and the piezoelectric elements 33b and 37 can simultaneously detect bending operation displacement. Therefore, the physical quantity sensor 400 can be used, for example, as a contact sensor.

Furthermore, since the first physical quantity detection section and the second physical quantity detection section can be integrated into one unit, it is possible to realize a smaller physical quantity sensor 400. Particularly, since the piezoelectric elements 33b and 37 of the second physical quantity detection section are laminated so as to be disposed on both sides of the piezoelectric element 33a of the first physical quantity detection section, it is possible to double the sensor sensitivity with respect to the bending force in the second physical quantity detection section despite being a small device.

Furthermore, since the electrode layer 32 is shared between the first physical quantity detection section and the second physical quantity detection section, the physical quantity sensor 400 can be made thinner. Furthermore, since the electrode layer 32 commonly used for the first physical quantity detection section and the second physical quantity detection section can be formed through one process, it is possible to easily produce the physical quantity sensor 400.

Modification Example

The present invention is not limited to the above-described embodiments and examples, but can be modified in various ways based on the spirit and scope of the present invention, and these are not excluded from the scope of the present invention. For example, the first physical quantity detection section 6 and the second physical quantity detection section 7 in the first embodiment share the electrode layer 2, but instead of the electrode layer 2, a first electrode layer and a second electrode layer independently formed for the first physical quantity detection section and the second physical quantity detection section respectively may be used.

Furthermore, the first physical quantity detection section and the second physical quantity detection section in the third embodiment above share the electrode layer 22, but a configuration may also be adopted in which an insulating layer and an electrode layer are formed sequentially from the top between the electrode layer 22 and the piezoelectric element 23b so that the electrode layer 22 is not shared. Similarly, a configuration may also be adopted in which an insulating layer and an electrode layer are formed sequentially from the top between the electrode layer 32 and the piezoelectric element 33b in the physical quantity sensor according to the fourth embodiment so that the electrode layer 32 is not shared between the first physical quantity detection section and the second physical quantity detection section.

Furthermore, in the first embodiment, if the electrode layer 2 has sufficient strength, a configuration without the substrate 1 may also be possible. Even in the case of the physical quantity sensor in a configuration without the substrate 1, it goes without saying that the configuration is maintained in which the thicknesses of the respective sections are adjusted so that the center line in the thickness direction of the first piezoelectric element matches the center line in the thickness direction of the first physical quantity detection section and at the same time the center line in the thickness direction of the second piezoelectric element does not match the center line in the thickness direction of the second physical quantity detection section.

Furthermore, a protective layer made of PDMS or the like may be provided on the surface of the electrode layer 14b in the second embodiment, the electrode layer 24b in the third embodiment or the electrode layer 38 in the fourth embodiment. Even in the case of the physical quantity sensor provided with the above-described protective layer, it goes without saying that the configuration is maintained in which the thicknesses of the respective sections are adjusted so that the center line in the thickness direction of the first piezoelectric element matches the center line in the thickness direction of the first physical quantity detection section and at the same time the center line in the thickness direction of the second piezoelectric element does not match the center line in the thickness direction of the second physical quantity detection section.

Figure 7:
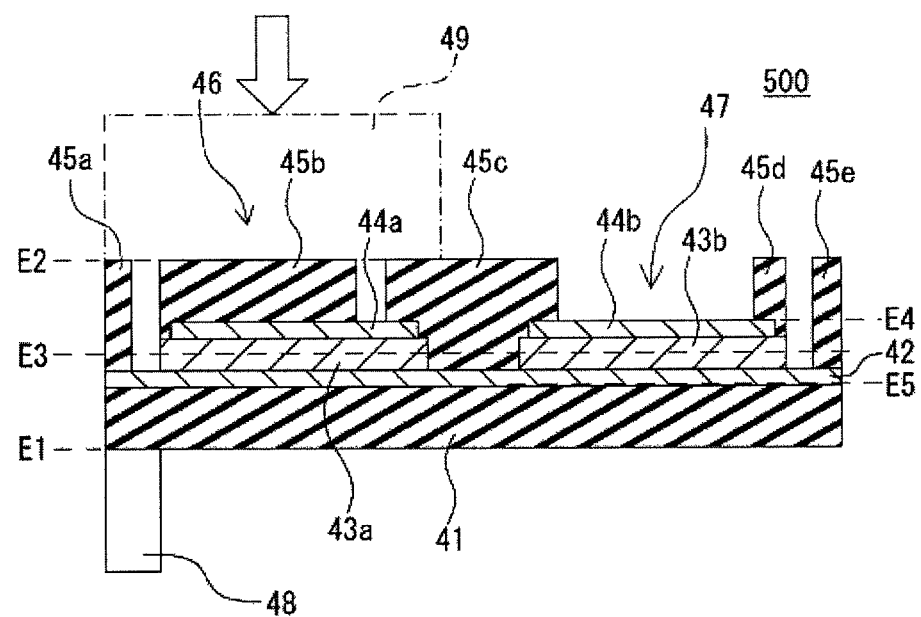
FIG. 7 is a cross-sectional view of a physical quantity sensor according to a modification example of the first embodiment of the present invention.

Furthermore, as shown in FIG. 7, one end of a physical quantity sensor 500 having the same configuration as that of the first embodiment is attached to a base 48 to form a cantilever and an object 49 is placed so as to come into contact with protective layers 45a, 45b and 45c of a first physical quantity detection section 46 and when a force in a direction shown by a white arrow in FIG. 7 is applied to the object 49, it is possible to detect pressure from the object 49 using a piezoelectric element 43a. Furthermore, when the object 49 vibrates in the vertical direction in FIG. 7, it is possible not only to detect pressure from the object 49 using the piezoelectric element 43a but also to detect vibration of the object 49 since a second physical quantity detection section 47 (piezoelectric element 43b) vibrates. Here, since regions denoted by reference numerals 41 to 47 are similar to the regions denoted by reference numerals 1 to 7 in the first embodiment respectively, descriptions thereof will be omitted. Furthermore, since positions E1 to E5 are similar to the positions A1 to A5 in the first embodiment respectively, descriptions thereof will be omitted. In the present modification example, if an electrode layer 42 has sufficient strength, the electrode layer 42 without using the substrate 41 may be used instead of the substrate, the electrode layer 42 may be directly attached to a base 48 to support the physical quantity sensor. However, even when the physical quantity sensor in the configuration without the electrode layer 42 is adopted, it goes without saying that the configuration is maintained in which the thicknesses of the respective sections are adjusted so that the center line in the thickness direction of the first piezoelectric element matches the center line in the thickness direction of the first physical quantity detection section and at the same time the center line in the thickness direction of the second piezoelectric element does not match the center line in the thickness direction of the second physical quantity detection section.

Furthermore, in the physical quantity sensors according to the above-described embodiments and modification example, regarding the degree of match between the center line in the thickness direction of the first piezoelectric element and the center line in the thickness direction of the first physical quantity detection section, a case with a complete match has been described above, but if not that high degree of detection accuracy of the respective physical quantities may be expected, the degree of match between the center line in the thickness direction of the first piezoelectric element and the center line in the thickness direction of the first physical quantity detection section may be a quasi-match (substantial match) level.

Furthermore, the physical quantity sensor according to the above-described embodiments and modification example is provided with a protective layer, but a protective layer need not be particularly provided if the electrode layer and piezoelectric element are made of a material sufficiently resistant to external forces. However, even in the case of the physical quantity sensor in the configuration with no protective layer, it goes without saying that the configuration is maintained in which the thicknesses of the respective sections are adjusted so that the center line in the thickness direction of the first piezoelectric element matches the center line in the thickness direction of the first physical quantity detection section and at the same time the center line in the thickness direction of the second piezoelectric element does not match the center line in the thickness direction of the second physical quantity detection section.

Furthermore, the second physical quantity detection section in the fourth embodiment is configured to have two piezoelectric elements 33b and 37 so as to have the sensor sensitivity with respect to bending double that in the case with one piezoelectric element, but the second physical quantity detection section may also be configured to have three or more piezoelectric elements so as to have the sensor sensitivity with respect to bending triple or more that in the case with one piezoelectric element. However, in the case of the physical quantity sensor in the configuration using three or more piezoelectric elements, it goes without saying that the configuration is maintained in which the thicknesses of the respective sections are adjusted so that the center line in the thickness direction of the first piezoelectric element matches the center line in the thickness direction of the first physical quantity detection section and at the same time the center line in the thickness direction of the second piezoelectric element does not match the center line in the thickness direction of the second physical quantity detection section.

DESCRIPTION OF SYMBOLS 1, 11, 21, 31, 41 Substrate
2, 4a, 4b, 12, 14a, 14b, 16, 22, 24a, 24b, 32, 34a, 34b, 36, 38, 42, 44a, 44b Electrode layer
3 Piezoelectric element layer
4 Conductive layer
3a, 3b, 13a, 13b, 23a, 23b, 33a, 33b, 33a, 37, 43a, 43b Piezoelectric element
5a, 5b, 5c, 5d, 5e, 25, 45a, 45b, 45c, 45d, 45e Protective layer
6, 46 First physical quantity detection section
7, 47 Second physical quantity detection section
15, 35 Insulating layer
48 Base
49 Object
100, 200, 300, 400, 500 Physical quantity sensor

What is claimed is:

1. A physical quantity sensor comprising:
a first physical quantity detection section having a first electrode layer, a first piezoelectric element provided on the first electrode layer and a second electrode layer provided on the first piezoelectric element; and
a second physical quantity detection section arranged side by side with the first physical quantity detection section and having a third electrode layer connected together with the first electrode layer, a second piezoelectric element provided on the third electrode layer and a fourth electrode layer provided on the second piezoelectric element, the second physical quantity detection section having a different configuration of at least one of the layers from that of the first physical quantity detection system, enabling the first and second physical quantity detection sections to simultaneously sense different physical quantities from the same environment while using a common structure,
wherein the first piezoelectric element is disposed so that a center line in a thickness direction of the first piezoelectric element substantially matches or matches a center line in a thickness direction of the first physical quantity detection section, and
the second piezoelectric element is disposed so that a center line in a thickness direction of the second piezoelectric element is disposed eccentrically with respect to a center line in a thickness direction of the second physical quantity detection section.

2. The physical quantity sensor according to claim 1, wherein the connection of the first electrode layer and the third electrode layer comprises part of the first electrode layer and part of the third electrode layer connected together so as to form one electrode layer.

3. The physical quantity sensor according to claim 1, wherein the second physical quantity detection section is laminated on at least one side of the first physical quantity detection section via a flexible insulating layer.

4. The physical quantity sensor according to claim 2, wherein the first electrode on the first piezoelectric element side is fixed to a substrate and the second piezoelectric element constitutes a cantilever oscillatable in a predetermined direction by external vibration.

5. The physical quantity sensor according to claim 1, wherein a polydimethyl siloxane substrate is provided on at least part of the surface.

6. A process for producing the physical quantity sensor according to claim 2, comprising:
a piezoelectric element forming step of laminating and then etching a piezoelectric element layer on the one electrode layer to form the first piezoelectric element and the second piezoelectric element; and
an electrode layer forming step of laminating and then etching a conductive layer on the first piezoelectric element and the second piezoelectric element to form the third electrode layer on the first piezoelectric element and form the fourth electrode layer on the second piezoelectric element.

7. The physical quantity sensor according to claim 2, wherein a polydimethyl siloxane substrate is provided on at least part of the surface.

8. The physical quantity sensor according to claim 3, wherein a polydimethyl siloxane substrate is provided on at least part of the surface.

9. The physical quantity sensor according to claim 4, wherein a polydimethyl siloxane substrate is provided on at least part of the surface.

* * * * *